United States Patent
Herrmann et al.

(10) Patent No.: US 9,277,767 B2
(45) Date of Patent: Mar. 8, 2016

(54) DEVICE FOR PRODUCING CIGARETTES IN THE TOBACCO PROCESSING INDUSTRY AND A METHOD THEREFORE

(75) Inventors: Rainer Herrmann, Hamburg (DE); Udo Schlemm, Hamburg (DE)

(73) Assignee: TEWS Elektronik GmbH & Co. KG, Hamburg (DE)

( * ) Notice: Subject to any disclaimer, the term of this patent is extended or adjusted under 35 U.S.C. 154(b) by 1180 days.

(21) Appl. No.: 13/177,229

(22) Filed: Jul. 6, 2011

(65) Prior Publication Data

US 2012/0006338 A1 Jan. 12, 2012

(30) Foreign Application Priority Data

Jul. 6, 2010 (DE) .......................... 10 2010 026 178

(51) Int. Cl.
*G01N 21/89* (2006.01)
*A24C 5/34* (2006.01)
*G01N 22/04* (2006.01)

(52) U.S. Cl.
CPC .............. *A24C 5/3412* (2013.01); *G01N 22/04* (2013.01)

(58) Field of Classification Search
CPC ............................... A24C 5/3412; A24C 5/005
USPC ..................................... 131/365, 58
See application file for complete search history.

(56) References Cited

U.S. PATENT DOCUMENTS

| | | |
|---|---|---|
| 6,020,969 A | 2/2000 | Struckhoff et al. |
| 6,645,605 B2 | 11/2003 | Hammersmith et al. |
| 2005/0172977 A1* | 8/2005 | Jadot et al. ................... 131/365 |
| 2005/0225332 A1* | 10/2005 | Schroder ...................... 324/636 |
| 2009/0025742 A1 | 1/2009 | Matsufuji et al. |
| 2009/0301506 A1 | 12/2009 | Kida et al. |
| 2011/0093212 A1* | 4/2011 | Herrmann et al. .............. 702/23 |

FOREIGN PATENT DOCUMENTS

| | | |
|---|---|---|
| DE | 202005010375 | 10/2005 |
| EP | 0791823 | 8/1997 |
| EP | 902277 | 3/1999 |
| EP | 1321049 | 6/2003 |
| EP | 1449447 | 8/2004 |
| EP | 2177118 | 4/2010 |
| WO | 02/43513 | 6/2002 |
| WO | 2004/057986 | 7/2004 |
| WO | 2008/146170 | 12/2008 |
| WO | 2009/027831 | 3/2009 |
| WO | WO 2009030314 A1 * | 3/2009 |
| WO | 2009/157720 | 12/2009 |

* cited by examiner

*Primary Examiner* — Galen Hauth
(74) *Attorney, Agent, or Firm* — Vidas, Arrett & Steinkraus

(57) ABSTRACT

A device for producing cigarettes in the tobacco processing industry that has a tobacco processing unit and a paper feeding unit, which feeds a paper having LIP strips to the tobacco processing unit, wherein the paper feeding unit has a measurement device, which continuously detects the LIP strips, wherein the measurement device has a microwave resonator, through whose measurement region the paper having the LIP strip is passing, and which detects a shift of the resonance curve and/or a broadening of the resonance frequency.

19 Claims, 2 Drawing Sheets

DEVICE FOR PRODUCING CIGARETTES IN THE TOBACCO PROCESSING INDUSTRY AND A METHOD THEREFORE

CROSS-REFERENCE TO RELATED APPLICATIONS

Not applicable

STATEMENT REGARDING FEDERALLY SPONSORED RESEARCH

Not applicable

BACKGROUND OF THE INVENTION

The present invention relates to a device for producing cigarettes in the tobacco processing industry and a method therefore.

US 2005/0172977 A1, the entire contents of which is incorporated herein by reference, discloses the production of tobacco products with a paper that has relatively low ignition properties. In technical language, such papers are designated as "low ignition propensity (LIP)" papers.

LIP paper is characterized in that the paper strips responsible for the LIP effect have a coating that confers the low ignition properties to the paper. These strips, as is known from WO 2009/157720 A2, the entire contents of which is incorporated herein by reference, for example, have a width of 5 mm and completely surround the cigarette. For producing such tobacco products, the initially named application US 2005/0172977 A1, the entire contents of which is incorporated herein by reference, describes that the LIP paper is unrolled from a roll and fed to a tobacco processing unit of the cigarette machine. In order to be able to conduct the feeding speed and the speed during cutting the processed endless tobacco rods into individual cigarettes corresponding to the LIP strips, the LIP paper has synchronization marks. An optically based marking sensor identifies the synchronization marks on the fed paper, and generates corresponding synchronization signals that control the speed of the subsequent processing steps so that the LIP strips of paper are in the desired position on the cigarette. Further, it is known from US 2005/0172977, the entire contents of which is incorporated herein by reference, to use LIP strips themselves as synchronization marks, and to detect these optically in order to generate synchronization signals for producing the cigarette strips. A disadvantage of optically identifying the LIP strips is that they can form a weak contrast and therefore cannot be optically identified with sufficient reliability.

From US 2009/0301506 A1, the entire contents of which is incorporated herein by reference, a method is known for producing a LIP cigarette paper. The LIP strips are applied as a coating to the cigarette paper.

From WO 2009/027831 A2, the entire contents of which is incorporated herein by reference, a cigarette paper is known that has a wave-like circumferential LIP band. Different shapes are proposed for the wave pattern.

From US 2009/0025742 A1, the entire contents of which is incorporated herein by reference, a LIP cigarette paper is known in which the LIP coating consists of a sodium alginate that is applied as an aqueous solution.

From WO 2008/146170 A2, the entire contents of which is incorporated herein by reference, LIP strips for cigarette papers are known that have a wave-like shape.

From EP 1 449 447 A1, the entire contents of which is incorporated herein by reference, a cigarette is known which has a greater tobacco density in a central core region than in the jacket region surrounding the core region.

From WO 02/43513 A1, the entire contents of which is incorporated herein by reference, a cigarette with LIP properties is known in which the glow of the cigarette is reduced in its diameter by cellulose additive so that the cigarette is self-extinguishing.

From U.S. Pat. No. 6,645,605 B2, the entire contents of which is incorporated herein by reference, a material for a cigarette with LIP properties is known in which a coating is applied on the cigarette paper by a thermoplastic polymer.

From EP 2 177 118 A1, the entire contents of which is incorporated herein by reference, a method for processing a LIP strip is known in which the material of the LIP strip is abraded in a positionally accurate manner for improving the adhesion properties.

BRIEF SUMMARY OF THE INVENTION

An object of the present invention is to provide a device for producing cigarettes and a method for that purpose that in a simple manner permits reliable detecting and inspecting of a LIP structure on the fed cigarette paper online/inline during the production process.

The invention relates to a device for producing cigarettes in the tobacco processing industry. Such a device comprises a tobacco processing unit and a paper feeding unit. The paper feeding unit feeds a paper provided with a LIP strip to the tobacco processing unit. When in the following reference is made to LIP strips, this is meant to be any structure on the cigarette paper that confers these LIP properties at least in regions. The measurement device of the paper feeding unit continuously detects the LIP strips of the fed cigarette papers. According to the invention, the measurement device has a microwave resonator, through whose measurement region the paper with LIP proceeds, and which detects a shift of the resonance curve and/or a broadening of the resonance curve.

The LIP strips can be checked online/inline based on the continuously detected measured values, in order to ensure their quality.

The use of microwave resonators in the tobacco processing industry is known per se. Such microwave resonators are used in the tobacco processing unit of the cigarette machine for determining the weight percent or the moisture of the cigarette. For this purpose, shifts of the resonant frequency and a broadening of the resonance curve are always detected and evaluated in a known manner. With the inventive device, a microwave resonator is used in the paper feeding unit. Also, its signals are not evaluated in the typical manner, in that for example, the quotient is considered with the shift of the resonance frequency and the broadening of the resonance frequency. The invention is based on the realization that with the use of LIP strips in cigarette papers the dielectric properties of the cigarette paper always changes in a measurable manner. This realization is independent of the precise material used for the LIP strips. According to the invention, signals of the microwave resonator for detecting the LIP strips in the cigarette machine are not evaluated in the typical manner, in which the ratio is formed of the shift of the resonance frequency and the broadening of the resonance frequency, rather the shift of the resonance frequency is evaluated independently of the broadening of the resonance curve, or vice versa. This evaluation allows very reliably detecting of the LIP strips by the microwave resonator at high speed in the cigarette machine.

In the preferred design of the device, the measurement device determines the distance between adjacent LIP strips from the continuously detected signals, and generates a warning signal if the detected distance exceeds a specified distance value or falls below a second specified value. In this design of the measurement device, it is checked whether the LIP paper is intact and whether the LIP strips were applied completely and in the correct distance on the paper. An error in the LIP paper, for example due to a missing LIP strip, is therefore identified and the appropriate cigarette can be subsequently rejected.

In a further preferred design, the measurement device creates from the continuously detected signals, synchronization signals for the tobacco processing unit. The tobacco processing unit, with the use of these synchronization signals, can control the correct feed of the LIP papers corresponding to the position of the rod and the knife, in order to guarantee that the LIP strips are located in a specified position on the cigarette.

In a further preferred design, the paper feeding unit feeds the LIP paper in a positionally accurate manner to the tobacco processing unit. This positionally accurate feeding guarantees that during later processing of the LIP paper into a cigarette, the LIP strips are located in the defined positions.

In a further expedient design, with the use of the synchronization signals, the paper feeding unit can subject the LIP paper to a further positionally accurate processing. From the initially mentioned document, EP 2 177 118 A1, the entire contents of which is incorporated herein by reference, it is known to treat a LIP paper using a laser beam in order to attain an improved adhesion behavior in specific regions of the cigarette. Such processing of the LIP paper presumes the precise knowledge of the position in which the LIP strip is located.

In a further preferred design, the measurement unit, using the continuously detected signals, can determine a mass or a mass per area for each LIP strip, and generate a warning signal if the determined mass or mass per area for the LIP strips exceeds a specific mass value and/or falls below a second specific mass value. In this manner, with the LIP paper, not only the distance between the LIP strips is checked, but alternatively, or additionally, a mass of the LIP strips can be checked, so that comprehensive quality control of the processed LIP papers is possible.

In a preferred design, the microwave resonator is designed as a planar sensor whose measurement region extends through the paper. Preferably this is a compact planar sensor that is disposed on the side of the paper facing away from the LIP structure, and whose measurement field detects the LIP structure through the paper. The compact planar sensor is open on the end, having a quarter wavelength lambda resonator whose open region can be designed very small, and whose geometric dimensions define the region of the measurement field. In this way, it can be achieved that its spatial resolution is smaller or the same as the width of the LIP strips, which move through the measurement field.

In a further expedient design, a cavity resonator is provided as the microwave resonator whose measurement region is located in a cylindrical or rectangular cavity. The bottom and top of the cylindrical or rectangular cavity are disposed so closely together, such that with installation of a slit, a spatial resolution can be attained that is smaller (equal) to the width of the LIP strips—assuming the resonator is operated in the basic mode. The cigarette paper to be measured is fed with its LIP strips through the measurement field in the cavity.

In a further expedient design, the microwave resonator is a gap sensor. The gap sensor is a laterally slit coaxial resonator that can also be opened on half its side, through whose opening slit the LIP paper tape can be fed. Because the diameter of the coaxial sensor has no substantial influence on the measurement frequency (only the length), the region of the field concentration can be dimensioned so small that the band passing through can be measured with a spatial resolution which is smaller or equal to the LIP strip width.

The objective according to the invention is also solved by the use of a microwave resonator.

According to the invention, the microwave resonator is used for online checking of LIP strips in paper. The paper is fed to a tobacco processing unit of a cigarette machine. The inventive microwave resonator detects a shift of the resonance frequency and/or broadening of the resonance curve, in order to detect the LIP strip on the paper that is fed. The use of a microwave resonator is based on the realization that with the processing of cigarette paper having LIP strips, detecting the dielectric properties through the microwave resonator is far superior to optically detecting the LIP strips, and in particular is suitable also for the demanding technical requirements of a cigarette machine.

In a preferred design of the invention, a distance between two adjacent LIP strips is detected and compared to a specific maximum distance and/or minimum distance. If the detected distance exceeds the maximum distance, a warning signal is generated. Likewise, if the detected distance falls below the minimum distance. The warning signal indicates to the tobacco processing unit in the cigarette machine that the distance of the LIP strips is too large so that specific distances of the LIP strips cannot be readily maintained.

In a further expedient design, synchronization signals are generated from the continuously detected signals of the LIP strips for the paper feeding unit. The synchronization signals permit the tobacco processing unit to perform the feeding of the LIP paper band synchronously to the production of the endless cigarette rod and to the cutting.

In a similar preferred use, the paper feeding unit feeds the LIP paper in a positionally accurate manner based on the synchronization signals of the tobacco processing unit. In this way it can guarantee that the LIP strips are provided in the specific position in the process cigarette.

According to the invention it is also provided that the LIP paper of the feeding unit is subjected to a further positionally correct processing using the synchronization signals.

In the inventive use of a microwave resonator for detecting the LIP strips in the cigarette paper, a mass or a mass per area can also be determined for each of the LIP strips, and a warning signal can be generated if the determined mass or mass per area exceeds or falls below the specific mass values for the LIP strips.

In a preferred design, a compact planar sensor is used as the microwave resonator, with a field distribution that is less than or equal to the width of a LIP strip. Alternatively, a cylindrical or rectangular cavity resonator, or alternatively a laterally slit coaxial resonator can be used as a microwave resonator, whose field distribution is less than or equal to the width of the LIP strip.

BRIEF DESCRIPTION OF THE SEVERAL VIEWS OF THE DRAWINGS

In the following, the invention is explained in more detail using the figures. They show.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
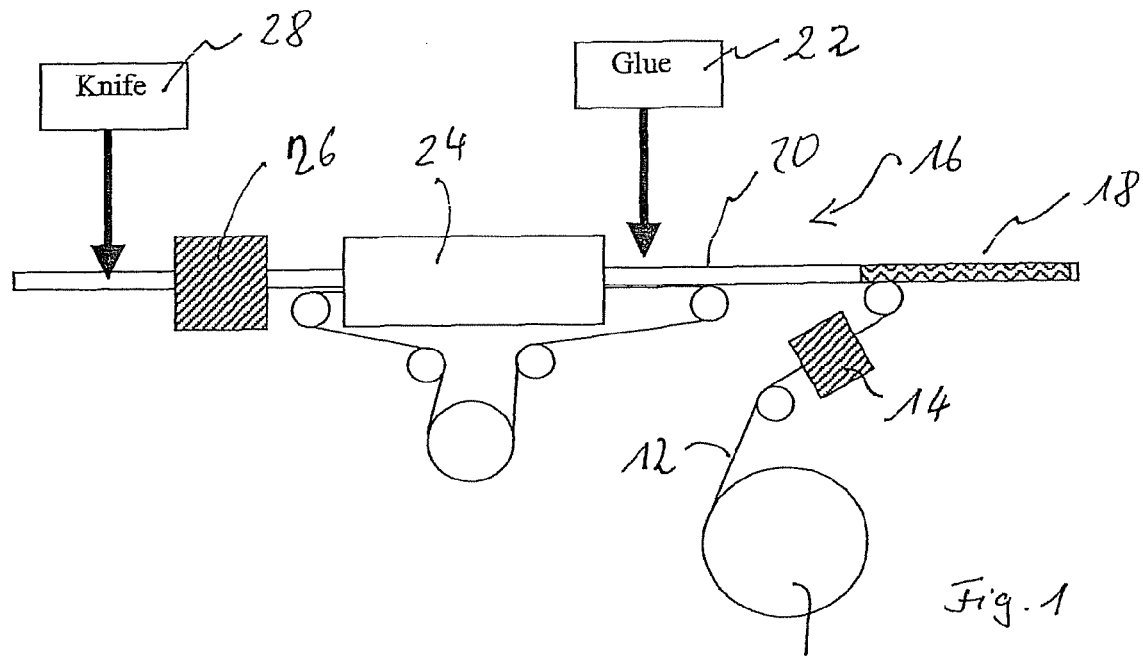
FIG. 1 a schematic view of a part of the cigarette processing machine with paper feed and tobacco processing, FIG. 2 a schematic view of a microwave cavity sensor for detecting LIP strips, FIG. 3 a mini planar sensor in a schematic view with its measurement field for detecting LIP strips, FIG. 4 the measurement values for a LIP cigarette paper collected in the cavity resonator, for example, and FIG. 5 the measurement values for a planar sensor recorded with a planar sensor, for example.

FIG. 1 shows, in a very simplified view, a cigarette machine that is fed cigarette paper 12 from a bobbin 10. The cigarette paper 12 passes through the measurement device 14 and thus arrives in the tobacco processing part 16 of the cigarette machine. Appropriately prepared tobacco 18 is combined with the cigarette paper 12 into an endless cigarette rod 20 that passes through a glue unit 22. The endless cigarette rod acquired in this manner is fed to a warming unit 24, wherein in 26 the mass profile of the cigarette is tested. Subsequently, the endless cigarette rod processed in this manner is cut by knife 28 into individual cigarettes.

Figure 2:
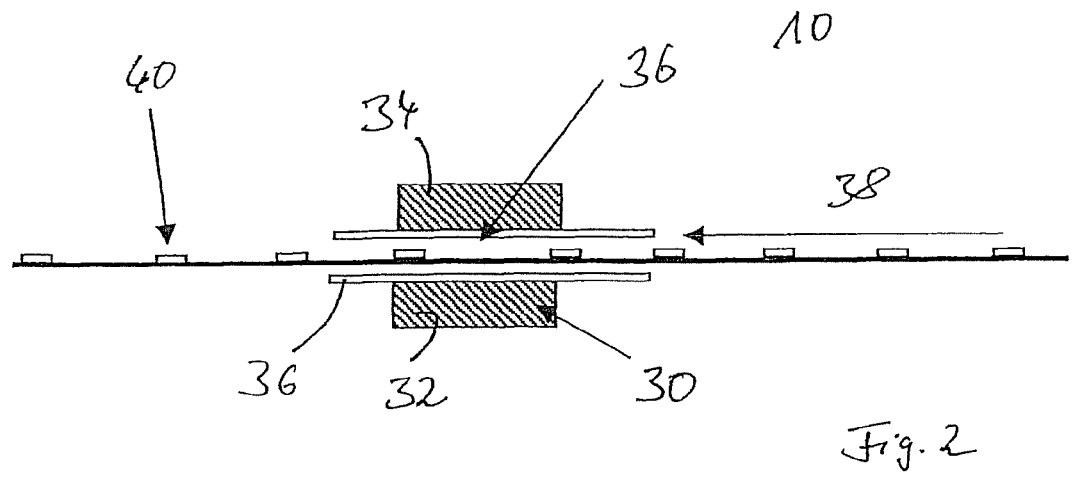

The measurement device 14 for the fed cigarette paper can consist of a cavity resonator, as shown in FIG. 2. The cavity resonator 30 consists of an upper housing part 33 and a lower housing part 34. The hollow cavity, in which the resonance to be measured is generated, is formed between the housing parts 32 and 34. Cavity resonators can be designed having separate upper and lower resonance parts 32 and 34; they are however, preferably one-piece or rigidly connected together, and the cigarette paper is fed through an appropriate slit in the wall through the resonator cavity. The slit can also be designed as a lateral opening of the cavity resonator for improved paper threading. For screening out undesired stray fields, the cavity is shielded by cover plates 36, which at each part of the resonator prevent the formation of stray fields outside of the resonator cavity. The cigarette paper is fed in direction 38 of the cavity resonator. The LIP strips 40 are schematically represented in FIG. 2 as raised strips. This is however by no means necessary, because LIP strips exist that are embedded in the cigarette paper and do not protrude.

Because the microwave resonator 30 detects the dielectric properties of the LIP strips, it is immaterial whether the LIP strips can be easily identified optically or are projecting from the cigarette paper.

Figure 3:
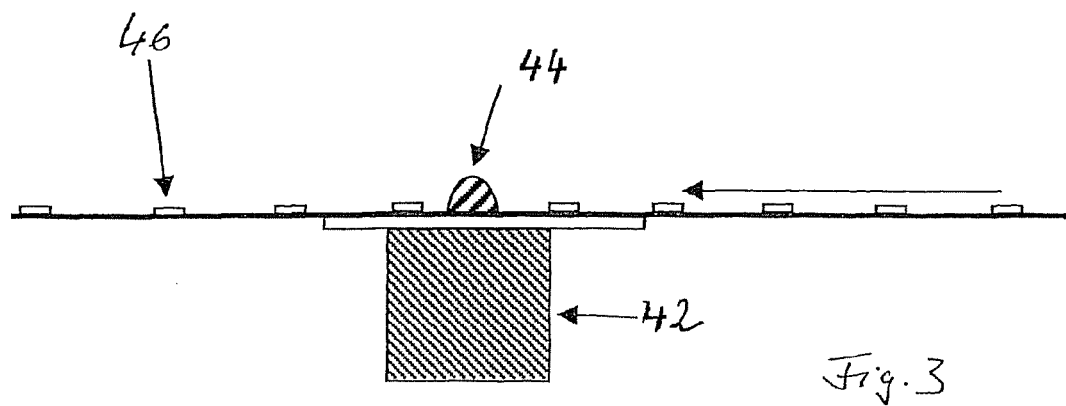

FIG. 3 shows the measurement device 14 from FIG. 1 in embodiments having a mini planar sensor 42 as an example of a compact planar sensor. The mini planar sensor 42 is disposed on one side of the cigarette paper, and has a measurement field 44 that projects from the mini planar sensor 42. The measurement field 44 detects dielectric changes due to the entering LIP strips 46. Using mini planar sensors, the changed dielectric properties, which lead to a shift of the resonance frequency difference and to a broadening of the resonance curve, are evaluated.

Figure 4:
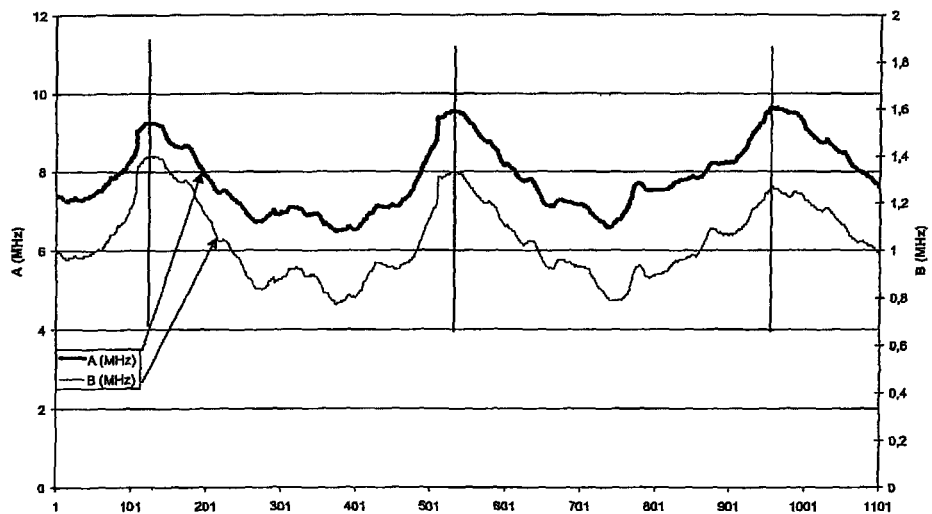

FIG. 4 shows as an example the change of the resonance frequency over time when the cigarette paper having LIP strips is fed through the cavity sensor. In FIG. 4 the change of the resonance frequency (measurement curve A) at a periodic structure with maximum and minimum can be seen clearly. In the maximum, in each case, a LIP script is present in the measurement area. The LIP scripts can also be detected alternatively or additionally by a so-called B value. The B value results from the broadening of the resonance curve. The B values are plotted as a measurement curve B. Again, it can be seen clearly that this curve shows the same periodic structure as shown in the A curve. Thus, evaluation of the A curve or the B curve can precisely determine the distance at which the LIP strips lie. Naturally it is also possible to evaluate both curves for reducing measurement errors. Likewise, based on the maximum of the A curves and/or the B curves, the position of the LIP strips can also be determined Additionally, the mass of the LIP scripts can be determined by the A curve and/or B curve, based on the difference in the measured values to the empty values and/or the values measured in the intermediate spaces between the LIP strips. On the other hand, through simultaneous evaluation of the A and B curves, the area mass of the applied LIP strip can be determined.

Figure 5:
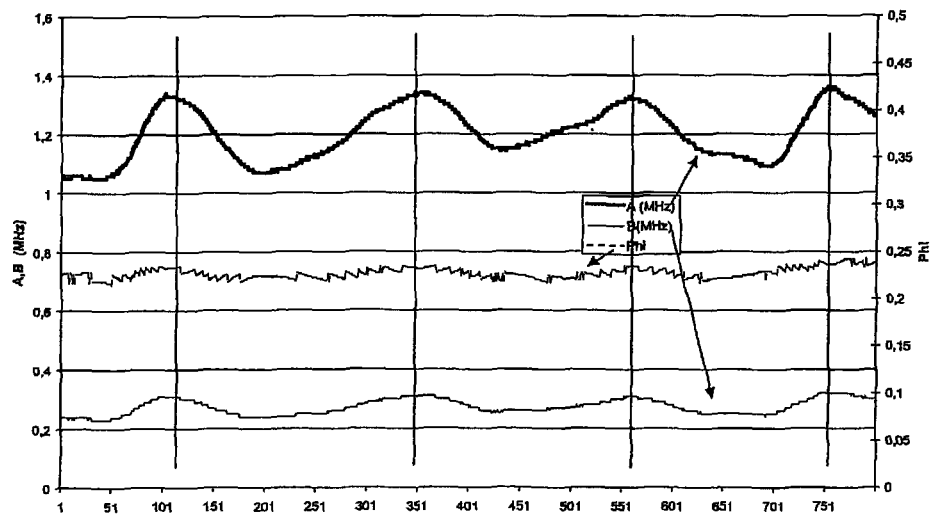

FIG. 5 shows the corresponding signals that were recorded by a mini planar sensor; still, the periodic structure of the LIP strips can be recognized again in the A curve and the B curve. Likewise, the Phi curve is plotted which calculates the quotient from A and B. As seen in FIG. 5, the Phi curve does not have a clear wave structure.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A device for processing cigarettes in the tobacco processing industry that has a tobacco processing unit and a paper feeding unit, which feeds a paper provided with LIP strips to the tobacco processing unit, the paper feeding unit having a measuring device, which continuously detects the LIP strips,
wherein the measurement device has a microwave resonator through whose measurement region the paper having the LIP strips is passing in the absence of tobacco, wherein the microwave resonator detects a shift of the resonance curve and/or a broadening of the resonance frequency, in order to check the LIP location of the strips on the fed paper.

2. The device according to claim 1, wherein the measurement device determines the distance between adjacent LIP strips from the continuously detected signals, and generates a warning signal if the determined distance exceeds a first specific distance value and/or falls below a second specific distance value.

3. The device according to claim 1, wherein the measurement device generates synchronization signals for the paper feeding unit from the continuously detected signals.

4. The device according to claim 3, wherein the paper feeding unit feeds the LIP paper to the tobacco processing unit in a positionally accurate manner.

5. The device according to claim 3, wherein the paper feeding unit feeds the LIP paper to a further processing unit in a positionally accurate manner using the synchronization signals.

6. The device according to claim 1, wherein from the continuously detected signals, the measurement device determines a mass or a mass per area for each of the LIP strips, and generates a warning signal if the determined mass or mass per area exceeds a first specific mass value for the LIP strips and/or falls below a second specific mass value.

7. The device according to claim 1, wherein the microwave resonator is designed as a planar sensor whose measurement region extends through the paper.

8. The device according to claim 1, wherein the microwave resonator is designed as a cavity resonator whose measurement region is located in the cavity.

9. The device according to claim 1, wherein the microwave resonator is constructed as a coaxial resonator.

10. A method of detecting a LIP strip, the method comprising:
provided a device for processing cigarettes in the tobacco processing industry that has a tobacco processing unit and a paper feeding unit, which feeds a paper provided with LIP strips to the tobacco processing unit, the paper feeding unit having a measuring device, which continuously detects the LIP strips,
wherein the measurement device has a microwave resonator through whose measurement region the paper having the LIP strips is passing in the absence of tobacco, wherein the microwave resonator detects a shift of the resonance curve and/or a broadening of the resonance frequency, in order to check the location of the LIP strips on the feed paper;
detecting a LIP strip, wherein the detecting comprises:
feeding into the paper feeding unit a paper comprising the LIP strip; and detecting the location of the LIP strip with the microwave resonator by detecting a signal comprising a shift of the resonance frequency and/or a broadening of the resonance curve.

11. The method of claim 10, the method further comprising:
comparing a distance between two adjacent LIP strips to a specific maximum distance and a specific minimum distance, and
generating a warning signal if the distance between two adjacent LIP strips exceeds the maximum distance and/or is less than the minimum distance.

12. The method of claim 10, the method further comprising:
generating synchronization signals for the paper feeding unit from the continuously detected signals of the LIP strips.

13. The method of claim 12, wherein the paper feeding unit, using the synchronization signals, feeds the LIP paper to the tobacco processing unit in a positionally accurate manner.

14. The method of claim 12, wherein the paper feeding unit, using the synchronization signals, subjects the LIP strips to a further positionally accurate processing.

15. The method of claim 10, the method further comprising:
detecting a mass or a mass per area for each of the LIP strips, and
generating a warning signal if the detected mass or mass per area for the LIP strips exceeds a specific first mass value or falls below a specific second mass value.

16. The method of claim 10, wherein the microwave resonator comprises a planar sensor, a cavity resonator, or a coaxial resonator.

17. A device for processing cigarettes, the device comprising:
a tobacco processing unit, and
a paper feeding unit structured and arranged to feed a paper provided with LIP strips to the tobacco processing unit, wherein the paper feeding unit comprises a measuring device, which continuously detects the LIP strips,
wherein the measurement device comprises a microwave resonator defining a measurement region through which the paper having the LIP strips passes, wherein the portion of paper within the measurement region is not in contact with tobacco,
wherein the microwave resonator comprises a detector structured and arranged to detect a shift of the resonance curve and/or a broadening of the resonance frequency, in order to determine the position of LIP strips passing through the measurement region.

18. The device for processing cigarettes of claim 17, wherein the microwave resonator comprises a slit though which the paper passes.

19. The device for producing cigarettes of claim 17 wherein the paper is introduced to tobacco after leaving the microwave resonator.

* * * * *